(12) United States Patent
Harley et al.

(10) Patent No.: US 8,431,146 B2
(45) Date of Patent: Apr. 30, 2013

(54) SCAFFOLD COMPRISING CO-PRECIPITATED COLLGEN AND GLYCOSAMINOGLYCAN FOR INHIBITING ADHESION OF BODY TISSUE LAYERS

(75) Inventors: Brendan A. Harley, Cambridge, MA (US); Eric C. Soller, Boston, MA (US); Eric Aiazian, Rotterdam (NL)

(73) Assignee: Axle International Ltd., London (GB)

( * ) Notice: Subject to any disclaimer, the term of this patent is extended or adjusted under 35 U.S.C. 154(b) by 309 days.

(21) Appl. No.: 12/725,656

(22) Filed: Mar. 17, 2010

(65) Prior Publication Data
US 2010/0166830 A1   Jul. 1, 2010

Related U.S. Application Data

(62) Division of application No. 11/683,393, filed on Mar. 7, 2007, now abandoned.

(60) Provisional application No. 60/779,762, filed on Mar. 7, 2006.

(51) Int. Cl.
*A61F 2/00* (2006.01)
*A61K 38/43* (2006.01)
*C12N 11/02* (2006.01)

(52) U.S. Cl.
USPC ........... 424/423; 424/426; 424/94.1; 435/177

(58) Field of Classification Search ........................ None
See application file for complete search history.

(56) References Cited

U.S. PATENT DOCUMENTS

| | | | |
|---|---|---|---|
| 6,133,325 A | 10/2000 | Schwartz et al. | |
| 2003/0225355 A1 | 12/2003 | Butler | |
| 2005/0177249 A1 | 8/2005 | Kladakis et al. | |
| 2005/0208095 A1 | 9/2005 | Hunter et al. | |

OTHER PUBLICATIONS

Butler, et al. Reduction of abdominal adhesions using composite collagen-GAG implants for ventral hernia repair. J Biomed Mater Res. 2001; 58)(1): 75-80.
O'Brien et al. The effect of pore size on cell adhesion in collagen-GAG scaffolds. Biomaterials. Feb. 2005; 26(4): 433-41.
Pieper et al. Development of tailor-made collagen-glycosaminoglycan matrices: EDC/NHS crosslinking, and ultrastructural aspects. Biomaterials. Mar. 2000; 21(6): 581-93.

*Primary Examiner* — David M Naff
(74) *Attorney, Agent, or Firm* — Haugen Law Firm PLLP

(57) ABSTRACT

A device for inhibiting adhesion of apposing human body tissue layers includes a scaffold having a designated mean pore size, relative density, and degradation half-life. The scaffold may be operably positioned between apposing tissue layers, such as proximate adhesiogenic layers at a wound site, so as to permit remesothelialization of the tissue without formation of fibrous adhesions. The scaffold device of the invention inhibits adhesion formation by promoting contractile cell migration away from the wound site for a predetermined period of time. The invention further relates to device and methods for promoting internal tissue regeneration, and for provision and/or dispensation of therapeutic and/or diagnostic agents in vivo.

3 Claims, 3 Drawing Sheets

SCAFFOLD COMPRISING CO-PRECIPITATED COLLGEN AND GLYCOSAMINOGLYCAN FOR INHIBITING ADHESION OF BODY TISSUE LAYERS

CROSS-REFERENCE TO RELATED APPLICATION

This application is a divisional of U.S. patent application Ser. No. 11/683,393, filed on Mar. 7, 2007, now abandoned and entitled "BIOACTIVE SCAFFOLD FOR THERAPEUTIC AND ADHESION PREVENTION APPLICATIONS", which itself claims priority to U.S. Provisional Patent Application Ser. No. 60/779,762, filed on Mar. 7, 2006, and entitled "BIOACTIVE SCAFFOLD FOR THERAPEUTIC AND ADHESION PREVENTION APPLICATIONS", the contents of which are incorporated herein in their entirety.

FIELD OF THE INVENTION

The present invention relates to the prevention of undesired tissue adhesion generally, and more particularly to devices for inhibiting tissue adhesion through diversion of fibroblast activities. The present invention further relates to methods and devices for therapeutic agent delivery, diagnostic agent delivery, and for promotion of tissue regeneration.

BACKGROUND OF THE INVENTION

The serosa comprises the outermost layer of the visceral structures that lie in the pleural and peritoneal cavities of the human body; it consists of a surface epithelial layer called mesothelium and is typically reinforced by irregular fibroelastic tissue or stroma. The serous cavities of the body are also lined by a single mesothelial layer of flattened cells (e.g. peritoneum, pleura, and pericardium).

When the serous or underlying vascularized layers of the human body are disrupted, either by a traumatic injury or a deliberate surgical procedure, the body mounts a complex inflammatory wound healing response to repair the defect. Initial trauma leads to increased histamine-mediated vascular permeability and bathing of the injured tissue's local environment in inflammatory exudates, resulting in traditional repair mechanisms characterized by mesothelial and fibroblast proliferation and, depending on the extent of injury, cell-mediated contraction. An early component of the spontaneous wound response is the formation of a fibrin matrix. Fibrin provides an initial structural framework necessary for mesothelial repair (also called remesothelialization) to occur via fibroblast proliferation. Under normal conditions, mesothelial repair proceeds concurrently with fibrinolysis, a component of the repair process that dissolves the fibrin matrix through the enzymatic action of plasmin. Both an inadequate blood supply and reduced tissue oxygenation are common in surgically traumatized tissue. Under these conditions, fibrinolytic activity is decreased and weak fibrinous bands, which often connect neighboring serosal surfaces, are allowed to persist under suppressed fibrinolysis. Over the 3 to 5 days following surgical injury, fibrinous bands gradually adopt and increase their cellularity, becoming organized by infiltrating fibroblasts via the deposition of collagen into strong fibrous bands, called adhesions. Adhesions predominate in a wide variety of in vivo sites (including, but not limited to, the peritoneal, pleural, and pelvic cavities) with similar mechanisms. In addition to surgical trauma, ischemia from surgical repair (grafting, suturing), the mechanical effects of handling, the presence of foreign materials (i.e. starch), inflammation-induced peritonitis, blood, and serosal drying may inhibit fibrinolysis and lead to adhesion formation.

Adhesion formation is a major complication of serosal repair following surgery, ischemia, or infection, and leads to conditions such as intestinal obstruction, severe abdominal pain, and infertility. Intraperitoneal adhesions, for example, occur in 67 to 93% of general abdominal surgeries and at an even higher rate following open gynecological pelvic surgeries. In addition to increased patient morbidity and mortality, adhesions present a significant burden to the health care system. Postoperative adhesions often require additional surgical procedures to remove obstructions and may increase the risk, cost, and complexity of future operations. Approximately 440,000 pelvic-abdominal adhesiolysis operations are performed in US each year. When adhesiolysis is performed to remove an intestinal obstruction, adhesions form again and create a new obstruction in 11 percent to 21 percent of cases. The annual cost of care for complications of post operative adhesions has been estimated to be $1.3 billion.

A detailed description of the pathogenesis and pathophysiology of post operative adhesion formation is presented elsewhere. It reveals that two main factors are required for adhesion formation: the continuous, close contact of two intraperitoneal structures (or one such structure and a denuded peritoneal mesothelium) as well as the presence of a fibrinous exudate in the wound site, usually resulting from a traumatic insult to a vascularized tissue layer. The fibrin deposition/degradation equilibrium has emerged as a crucial factor in adhesion formation. Under continued suppressed fibrinolytic activity, the fibrin matrix begins to represent vascular granulation tissue containing cellular elements. Beginning as early as the third post-operative day, the fine threads of fibrin are invaded by fibroblasts and organized through the deposition of collagen into mature, strong, fibrous adhesions. It is clear that neighboring tissue structures will not form permanent adhesions unless they can achieve continuous, close apposition. In addition, the cellularity of the fragile fibrin matrix connecting two such structures seems to represent a critical factor in adhesion maturation. The extent of fibroblast invasion ultimately determines whether the fibrin bridge is absorbed or persists and is organized, forming an adhesion.

As mentioned already, infection may be an important complication of the wound or injury healing. Currently antibiotics and other agents are widely used for the treatment or prophylactics of infection, mostly as a powder or a spray applied over the surgical wound area before the closure. These methods of drug delivery are simple but have a disadvantage of very fast clearance of the drug from the treatment area to other areas and therefore suboptimal spatial and temporary drug concentration and distribution patterns in the cavity. There also is a wide variety of drug delivery formulations and devices suggested for the local drug delivery into the wound area. However, these products are usually preparations which are produced already containing a specific drug agent and in addition to that often contain a binding agent to contain and regulate the drug release; they are also often made of materials which do not occur naturally in a human body and have delayed or incomplete clearance from the human body when implanted. Furthermore, collagen-based drug delivery systems had been suggested with the use of liquid collagen, wherein cross linking of the liquid collagen was suggested to be performed within the body after the injection. Such a technique, however, has several disadvantages: (1) injection of a collagen form which is not naturally present in a human body; (2) injection of a cross-linking substance which is another unnatural agent; and (3) such technology is suitable for the intramural and subcutaneous delivery, but not convenient for use in surgical procedures involving body cavities and internal surgery.

There has been no report to date of a method that is unequivocally effective at preventing fibrous adhesion formation. However, numerous strategies have been evaluated in clinical settings. Such strategies include: (1) the use of biodegradable membranes or gels (also called mechanical barriers) to mechanically separate organs at the end of surgery; (2) the administration of therapeutic agents (e.g. NSAIDS, fibrinolytic agents, corticosteroids, antibiotics); and (3) performing laparoscopic (keyhole) surgery, which reduces the size of the incision and the extent to which organs are handled.

These existing methods are not without drawbacks. While select therapeutic agents have demonstrated an ability to reduce adhesion formation through their ability to alter various portions of the inflammatory wound healing response, these drugs are rapidly cleared from the wound site, which decreases their overall effectiveness during the approximately week-long fibrous adhesion formation process.

Mechanical barriers pose a potentially elegant solution to adhesion prevention. A successful barrier temporarily prevents apposition of serosal tissue surfaces by separating the adhesiogenic tissue while the normal tissue repair process occurs. Subsequent degradation and clearance of the substance from the body prevents a foreign body response involving fibrosis of the implant or local toxicity. An ideal barrier should be safe, effective, nonimmunogenic, noninflammatory, separate adhesiogenic tissue for the duration of the remesothelialization process, biodegrade, and remain functional in the presence of blood products. Further, the material should not interfere with the healing process, nor should it promote infection or abscess formation. Finally, it must inhibit the formation of adhesions while exhibiting ease of surgical use with respect to handling, application, retention at the wound site and applicability to both open and minimally invasive surgical procedures and facilitate combination with local drug application when necessary. To date the ideal barrier has yet to be developed.

A number of adhesion prevention products (mostly mechanical, biodegradable barriers) have been approved by the U.S. Food and Drug Administration (FDA) for demonstrating an ability to reduce the incidence of scarring and adhesion formation following surgery (one example, approved in 1997, is SepraFilm®, which is a synthetic biodegradable membrane). The International Adhesions Society website lists at least 12 products that have been approved by the FDA to date.

Anti-adhesion mechanical barriers that are commercially available are mostly synthetic polymeric membranes or films. Many of these products have demonstrated a degree of effectiveness but have several common drawbacks with regard to surgical use or clinical complications. SepraFilm® (carboxymethylcellulose/hyaluronic acid) has documented handling difficulty and may result in intraperitoneal abscesses due to differences in clearance of its polymeric components (i.e. fragmentation of film). Interceed® (oxidized regenerated cellulose) requires meticulous hemostasis in order to function properly and the material is prone to retention at the tissue surface. Gore-tex Surgical Membrane®. (expanded polytetrafluoroethylene) is difficult to handle during laparoscopy, does not biodegrade and may require additional surgery for removal, introducing the possibility of additional adhesion formation. The safety and efficacy of newer barrier methods including Sepracoat® (hyaluronic acid gel), ferric hyaluronate, cross-linked hyaluronic acid (Incert®), and photopolymerized hydrogels is not yet known.

While these barriers endeavor to prevent the close, continuous physical contact of adhesiogenic and neighboring serosal surfaces, they do not by their nature address the key cellular aspect of the wound response that is responsible for fibrous adhesion maturation: the migration of fibroblasts into the fibrin gel matrix and its subsequent organization into a fibrous adhesion via collagen synthesis.

Scaffolds are a relatively new class of biomaterials that are utilized widely in applications of regenerative medicine. They are highly porous, degradable macromolecular solids with specific microstructural characteristics. Following irreversible injury (injury of a severe enough nature that under normal spontaneous repair processes would result in scar, or non-physiological, tissue formation), scaffolds of highly specific structure and chemical composition have been shown to induce partial regeneration in several organs, notably skin and the peripheral nerves. Induced organ regeneration, or the recovery of physiological structure and function of non-regenerative tissues at the original site of injury (de novo synthesis) was accomplished using scaffolds that simultaneously blocked myofibroblast-generated contraction (the dominant method of spontaneous wound closure in adults) while mimicking the in vivo extracellular matrix environment (particularly the stroma) of the organ of interest.

Graft co-polymers of type I collagen and a glycosaminoglycan (chondroitin-6-sulfate) that were shown to actively block contraction in skin wounds (and induce regeneration) have structural properties that accomplish three main processes: 1) reduction of TGF-$\beta$ in the wound site, leading to downregulation of fibroblast (and contractile myofibroblast) recruitment following severe injury; 2) blocking orientation of myofibroblast axes in the plane of the defect where macroscopic contraction is observed; and 3) ensuring that the scaffold's contraction blocking properties persist for the duration of the interim myofibroblast contractile response but not so long as to interfere with key regenerative processes.

Importantly, collagen-GAG copolymers are effective templates for regeneration of the dermis, peripheral nerve, and conjunctiva and show promise in cartilage repair studies. The use of these analogs of the extracellular matrix has been linked to partial regeneration of the above organs, elimination of scar tissue, and a clear ability to block the contraction of fibroblasts in the wound site. Furthermore, these matrices are widely used as substrates to probe the local environment of connective tissue cell-mediated contraction and specifically, myofibroblast-mediated contraction. These scaffolds successfully induce tissue regeneration and impart contraction-blocking activity by altering the local environment of the contractile cells (fibroblasts) responsible for tissue contraction and scar formation.

SUMMARY OF THE INVENTION

By means of the present invention, undesired adhesion of apposing human body tissue layers may be inhibited so as to promote the remesothelialization of normal body tissue at a wound site. In one aspect of the invention, a device is provided for inhibiting such adhesion of apposing human body tissue layers, wherein the device includes a scaffold that is prepared by co-precipitation of collagen and a glycosaminoglycan, followed by lyophilization.

In another aspect of the invention, the device for inhibiting adhesion of apposing human body tissue layers may include a scaffold having a mean pore size of between about 5 and about 200 μm, a relative density of between about 0.5 and about 10%, and a degradation half-life of 1-6 weeks when disposed in vivo.

In a further aspect of the invention, a device is provided for the promotion of tissue regeneration, and particularly the regeneration of internal organ tissue.

The scaffold device of the invention may include a dispensable therapeutic agent for dispensation within the body. Such dispensation may, for example, be directed over time to an injured body tissue so as to promote efficient regeneration thereof.

The device of the invention may be utilized by being operably positioned between the apposing tissue layers, and acts to inhibit formation of fibrous adhesions by promoting contractile cell migration away from the wound site for a predetermined period of time.

The scaffold device of the invention may include a diagnostic agent that may or may not be dispensed from the scaffold. Such a diagnostic agent may be, for example, a radioactive marker material, an ultrasonic marker material, a magnetic marker material, and the like.

DETAILED DESCRIPTION OF THE PREFERRED EMBODIMENTS

The objects and advantages enumerated above together with other objects, features, and advances represented by the present invention will now be presented in terms of detailed embodiments described with reference to the attached drawing figure which is intended to be representative of various embodiments of the invention. Other embodiments and aspects of the invention are recognized as being within the grasp of those having ordinary skill in the art.

We now describe scaffolds that, by virtue of possessing novel, specific features, are capable of reducing the formation of fibrous adhesions after any type of internal injury by serving as a degradable, bioactive barrier (substances that physically prevent apposition of adjacent adhesiogenic and serosal surfaces while remesothelialization occurs). The bioactive nature of the scaffold additionally modifies the local environment and behavior of the contractile cells responsible for fibrous adhesion maturation and scar formation, mediating the organized wound contraction and aiding in the wound healing process in a manner which previously described bather products and membranes do not. The therapeutic anti adhesive scaffold (TAS) of the invention significantly reduces adhesion formation by actively promoting fibroblast migration away from the wound site (adhesiogenic surfaces, e.g. suture lines) and into the TAS.

Figure 1:
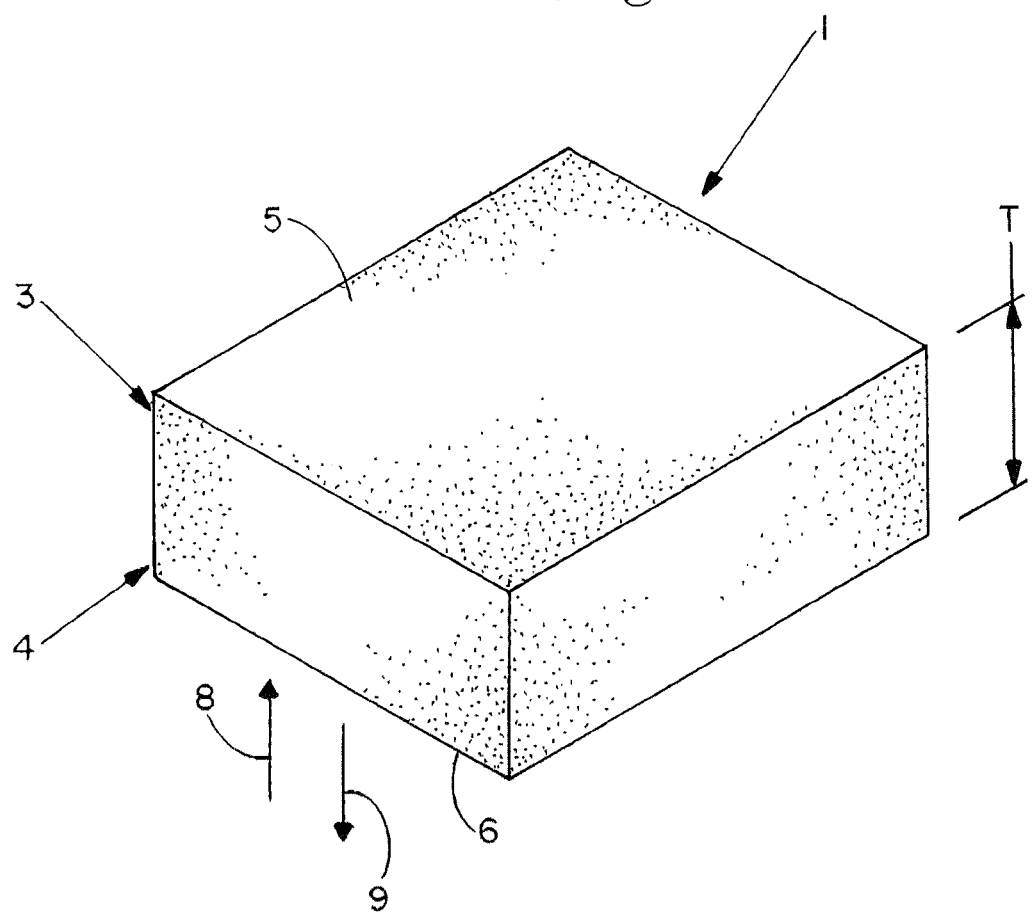
FIG. 1 is a perspective view of a scaffold device of the present invention.

As illustrated in FIG. 1, a TAS scaffold 1 has an upper portion 3 including an upper surface 5 and a lower portion 4 including a lower surface 6. In one operating orientation of TAS scaffold 1, lower surface 6 is placed into contact with the target tissue surface (such as the injured tissue). In such an orientation, exudate and cell flow from the injured tissue flows into TAS scaffold 1 generally in the direction illustrated by arrow 8. In some embodiments, TAS scaffold 1 may be provided with a releasable therapeutic agent, wherein such therapeutic agent may be released in a predetermined manner from TAS scaffold 1. Such therapeutic agent release may, for example, include release in the direction of arrow 9 to an injured tissue surface.

The structure of the scaffold allows it to serve as a depot for one or more therapeutic agents, for example by immersing the scaffold into the therapeutic agent instead of pure saline solution before implantation. The therapeutic agent may also be incorporated with the scaffold through chemical bonding or other techniques which provide at least temporary adherence of the therapeutic agent to or within the scaffold structure. Although it is not required, the structure of the TAS may be modified in such a way that the lower part of the TAS that comes into contact with the injured surface has higher permeability than the upper part and thus allows preferential optional therapeutic agent outflow from the TAS into the underlying wound area and inflow of exudate and cells through the lower part of TAS into the scaffold structure.

In addition to serving as a depot for therapeutic agents, the TAS scaffold of the present invention may additionally or instead at least temporarily retain a diagnostic agent thereat. Diagnostic agents may include, for example, materials that aid in remotely diagnosing conditions within the body. Such materials may include, for example, radioactive marker materials, magnetic marker materials, ultrasonic marker materials, and the like. The diagnostic materials contemplated for use in connection with the scaffold structure of the invention may optionally be dispensable from the structure, but may instead be retained at the scaffold for a predetermined period of time, including for example, the duration of the lifespan of the scaffold. Such diagnostic materials may aid in the monitoring of the physical condition of the scaffold, the extent of degradation of the scaffold, the extent of healing of damaged tissue, or other conditions throughout the body.

In embodiments of TAS scaffold 1 involving a dispensable agent, whether therapeutic, diagnostic, or both, such dispensation may be accomplished in a predetermined manner. For example, the dispensation of the respective agent or agents may be accomplished over a predetermined period of time at homogeneous or heterogeneous rates. Those of ordinary skill in the art will readily understand that modifications to the scaffold structure and/or the use of various binding agents, suspensions, solvents, or other materials can customize the rates of agent dispensation. Moreover, dispensation may be controlled as a function of the rate of scaffold biodegradation. It is to be further understood that various modifications may be made to TAS scaffold 1 in order to alter the degradation rate of the scaffold structure as a whole, or for only a portion of the scaffold structure. Thus, the therapeutic and/or diagnostic agent release may be coordinated with the biodegradation of part or all of the scaffold structure.

Although TAS scaffold 1 may be constructed in a variety of shapes and dimensions, one useful embodiment of TAS scaffold 1 may have a thickness dimension "T" of between about 0.1 and 10 mm. TAS scaffold 1 may also be dimensioned to superimpose the region of injured tissue. In addition, some embodiments of TAS scaffold 1 may have a Young's modulus value in a dry condition of between about 25-35 KPa. In hydrated form, one embodiment of TAS scaffold 1 may have a Young's modulus value of between about 0.1-0.5 KPa. While the above values for elasticity of the scaffold structure have been demonstrated to be useful, it should be understood that such values are not limiting to the structure of the present invention.

The mechanism for adhesion prevention is as follows. The TAS constitutes a barrier to adhesion formation by preventing the close, continuous contact of adhesiogenic surfaces through its placement over the area of surgical repair, thereby preventing the fibrin gel matrix from connecting neighboring structures. The TAS persists in its active state for a pre-determined time period that matches the remesothelialization phase and the duration of the fibroblast response during adhesion maturation before degrading completely through the body's normal enzymatic activity.

The TAS prevents adhesion formation by modifying the native behavior of fibroblasts at the wound site, the protagonist cell in the crucial step of fibrous adhesion maturation and scar formation. The material is highly porous and possesses an interconnected open pore microarchitecture that is well-suited for fibroblast migration and remodeling. Fibroblasts, originally recruited to the site of surgical repair through the spontaneous healing response (cytokines and the inflow of inflammatory exudate) recognize and bind avidly to the collagen ligands of the TAS, eventually migrating into and remodeling the TAS. Inflammatory exudate and blood products infiltrate the scaffold without compromising its function, bringing additional oxygen and nutrients into the porous structure, and further driving migration and persistence of fibroblasts in the scaffold for the period of time that the scaffold is active in the wound site prior to degradation. The pore volume fraction of the TAS is such that a very large number of ligands, or areas for fibroblast attachment, are present. Duration of the TAS in an undegraded state for the first 14 days after injury prevents apposition of the serosal tissues until such time that normal repair has occurred and the fibroblast response has been blocked.

In addition to adhesion prevention, the TAS has the potential to improve the quality of regeneration at the site of the surgically repaired defect and reduce macroscopically-observed post-surgical organ deformation. The net migration of contractile fibroblasts out of the plane of the defect and into the TAS reduces the incidence of contraction and scar synthesis at the wound site. Experimentally, the observed migration of myofibroblasts out of the wound plane and into a collagen-GAG copolymer scaffold has corresponded to an increase in the quality of regeneration of several organs.

Example

Figure 2:
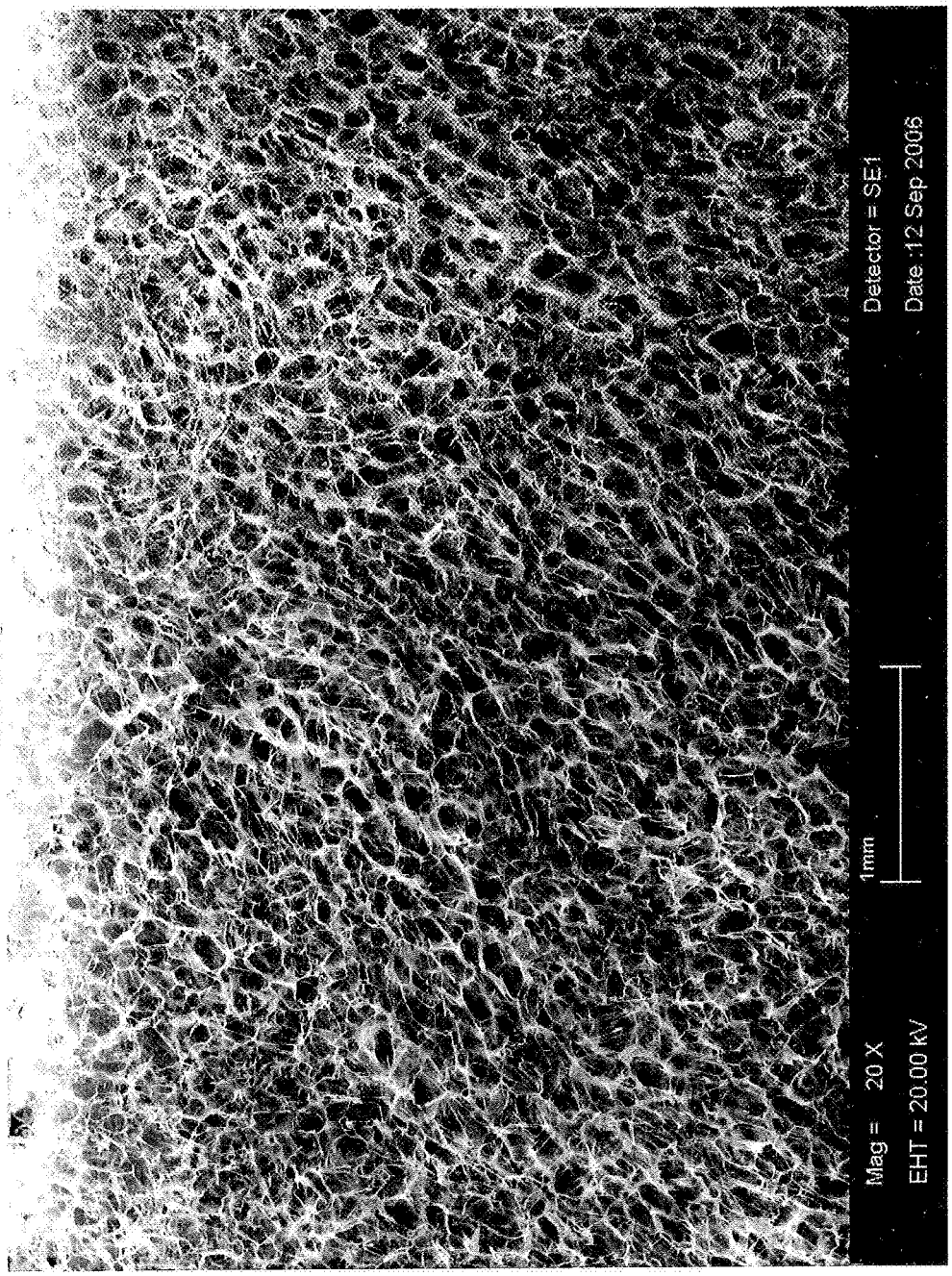
FIG. 2 is a magnified view of a scaffold device of the present invention.
Figure 3:
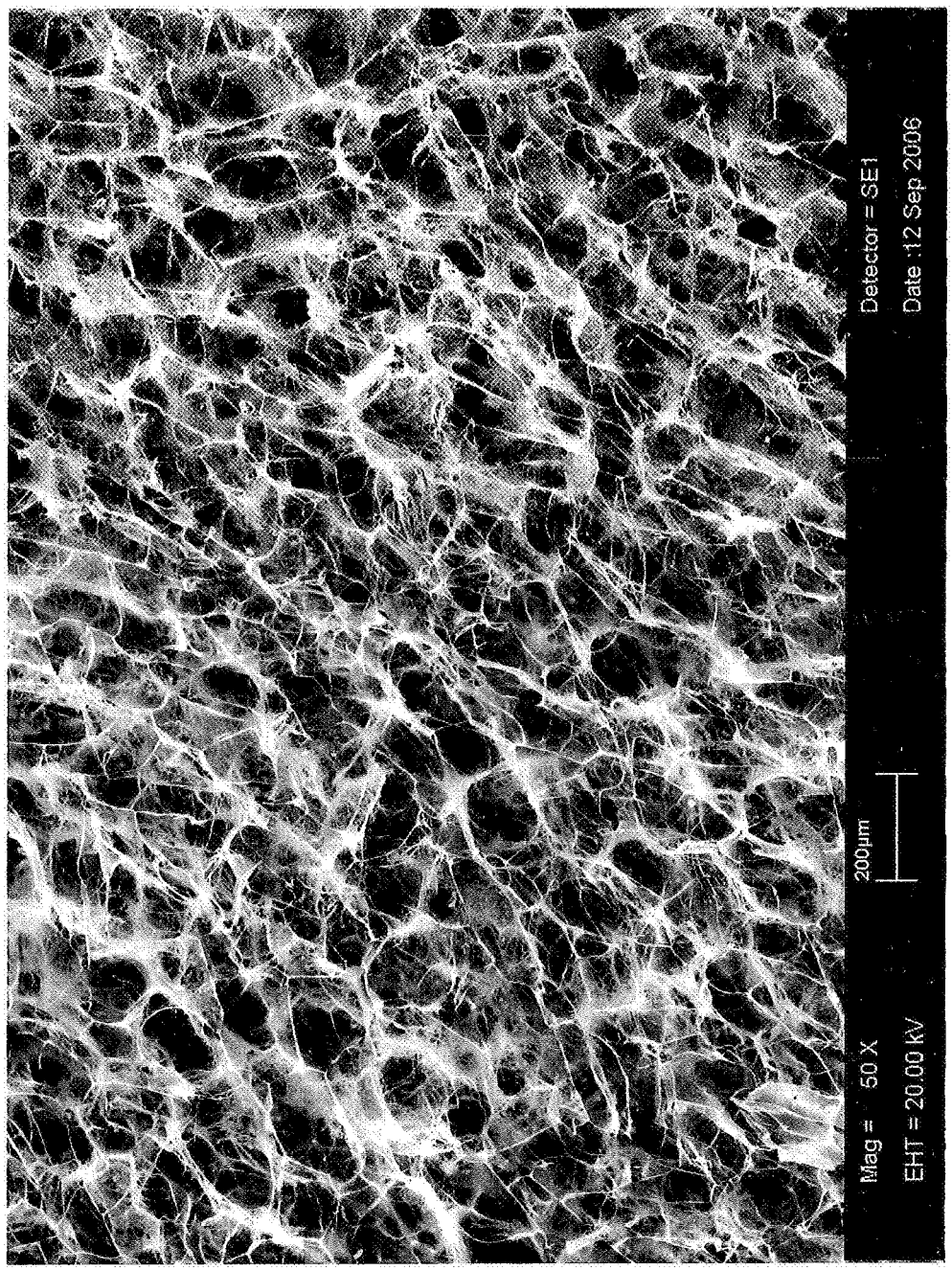
FIG. 3 is a magnified view of a scaffold device of the present invention.

The TAS is a highly porous, three-dimensional thin sheet or "scaffold" that is prepared by co-precipitation of collagen and a glycosaminoglycan (e.g. chondroitin-6-sulfate), followed by lyophilization. The relevant properties of the TAS (including, but not limited to, its anti-adhesive, bioadhesive, bioresorptive, antithrombogenic and physical properties) can be modified by adjusting the chemical composition, pore size, pore volume fraction, degree of cross-linking, and TAS thickness to yield a scaffold variant that is designed to suit the specific needs of a wide array of wound sites. The initial incarnation of the TAS scaffold is a collagen-glycosaminoglycan (GAG) scaffold with a mean pore size between 5 and 200 µm, preferably between 20 and 150 µm; relative density of 0.5-10%, preferably 0.5-5%; and a degradation half life of 1-6 weeks, preferably 1-4 weeks. Scanning electron microscope photographs taken of a TAS scaffold in accordance with this example are shown in FIGS. 2 and 3. FIG. 2 is a 20× magnification, while FIG. 3 illustrates a 50× magnification.

Collagen-GAG scaffolds can be crosslinked using a variety of methods that impart sterility and control over the in vivo degradation rate of the scaffolds, or alternatively can be sterilized by any number of processes including, but not limited to, ethylene oxide treatment, or gamma radiation. After fabrication, the TAS can be stored in a desiccated environment for extended periods of time without a decrease in bioactivity, making the TAS appropriate for large-scale fabrication and distribution. Processing conditions readily allow additional modification of micro-structural, compositional, and mechanical properties of the TAS. The TAS scaffold can be readily cut in the operating theater so that the surgeon can fit the scaffold to a particular wound or surgical site.

An example of how the therapeutic anti adhesive scaffold (TAS) can be used to prevent fibrous adhesion formation following surgery is for use following a routine partial colectomy (resection of the colon) and subsequent bowel anastomoses. In such a case, a laparotomy is performed with a median incision. Colotomy on the cecum and a single-layer repair of the bowel wall is performed. The TAS is placed on the cecal suture line and under the laparotomy incision before abdominal closure, forming a barrier between the suture lines and the serosal surfaces of the peritoneal cavity.

Sterile, hydrated sections of scaffold (hydrated in phosphate buffered saline solution, 30 minutes; a drug may be added to the solution at the discretion of the physician for the delivery to the wound site) that have been cut to the required size and shape are applied by the surgeon on the cecal suture line and under the laparotomy incision prior to surgical closure of the abdomen and sutured in place, ensuring close contact with the underlying adhesiogenic surface. The physical properties of the TAS are such that it may be simply applied to the site or if necessary fixed in place using variety of methods including, but not limited to, suturing, stapling, or gluing without detriment to its structural integrity or adhesion-prevention function.

Following surgical closure, the porous TAS becomes bathed in residual inflammatory exudates from the surgical repair and the peritoneal closure and become invaded with fibroblasts which recognize and bind avidly to the collagen ligands of the scaffold. Fibroblasts remodel the TAS for a period of 5-7 days, approximately matching the duration of the remesothelialization process. During this time, the TAS remains intact, providing a mechanical barrier and preventing continuous, close apposition between the colonic wound site and the regenerating mesothelium of the peritoneal wall. The half life of the TAS is such that it accomplishes regeneration of mesothelial layers without formation of fibrous adhesions or a chronic foreign body response (e.g. fibrous encapsulation), likely 1-4 weeks. The degradation characteristics of the TAS can be modified by variable cross-linking without significantly modifying the microarchitecture or mechanical characteristics of the scaffold, such that complete degradation times of substantially less than one week, or up to one year or more, may be obtained. In addition, the degradation of the TAS may be optionally homogeneous or heterogeneous, wherein one or more portions of the TAS may degrade at respectively different rates, and/or may respectively degrade to various extents.

Although not a required feature, the TAS may be modified to have an area with properties that differ from the rest of the TAS. These modifications include but are not limited to increased thickness and increased density. These may be particularly used for fixing the scaffold in place as well as maintaining the shape of the scaffold and modifying its depot qualities.

When required by the surgeon (such as in the case of severe injury to both apposing tissue layers), multiple pieces of TAS may be used simultaneously (e.g. one TAS may be applied to each of two apposing tissue surfaces). In this example, the TAS microarchitecture may be modified such that one side of the TAS is more bioadhesive than the other side. This ensures the TAS will prevent adhesion formation and decreases the likelihood of two apposing pieces of TAS from adhering to each other.

Although it is not required, the TAS may be provided with any number of a wide range of therapeutic agents, including, but not limited to, antibiotics, cytokines, cytostatic agents, fibrinolytic agents, corticosteroids, and non-steroidal anti-inflammatory drugs, prior to implantation. The porous nature of the TAS allows it to hold liquid agents much in the way a traditional sponge holds water and deliver them to the area of injury over time.

In general, the TAS comprises a biodegradable implant that, when placed or grafted between apposing serosal layers of adhesiogenic tissue, reduces the incidence and severity of fibrous adhesion formation between these tissues In addition to those described above, these therapeutic anti adhesive scaffolds possess the following features:

(i) The TAS represents a barrier to adhesion formation with an inherent capacity to prevent the close, continuous contact of adhesiogenic tissue and other serosal layers.

(ii) The bioactive nature of the TAS reduces irreversible components of the normal healing response (fibrous adhesion and scar formation) while promoting regeneration of mesothelial layers and reducing macroscopically observed organ deformation. The structural and chemical properties of the TAS (interconnected pore microstructure, high specific surface area, and chemical composition) modify the local extracellular environment and influence behavior of the contractile cells responsible for fibrous adhesion maturation and scar formation in a specific manner which previously described barrier membranes do not. The TAS significantly reduces adhesion formation by actively promoting fibroblast migration away from the wound site (adhesiogenic surfaces, e.g. suture lines) and into the porous TAS.

(iii) The TAS is a generic adhesive barrier scaffold with therapeutic properties that can be applied in response to injury in the human body resulting from processes including, but not limited to, surgical or traumatic injury, inflammation, and infection. The TAS may be applied at multiple sites including, but not limited to: organs of the peritoneal cavity, pericardium, pleural cavity, pelvic cavity, tendons, and nerves.

(iv) The TAS has a three-dimensional shape and mechanical properties such that it is an optimal type of implant for surgical application (e.g. pliable, sheet form, elastic properties). These properties allow the TAS to be modified easily in the operating room theater (e.g. trimmed to fit specific shapes and sizes).

(v) The structure of the implant is a highly porous scaffold fabricated through, for example, a co-precipitation reaction of collagen and possibly a glycosaminoglycan followed by lyophilization. Other fabrication techniques may be employed for the development of a scaffold structure. For example, a porous scaffold structure may be fabricated from collagen alone, or from collagen-GAG with various cross-linking agents.

(vi) All components of the TAS are naturally occurring structural materials of the human body that are degraded and cleared from the site of implantation through normal enzymatic action (collagenases).

(vii) The chemical composition, pore structure, pore size, pore volume fraction, degradation rate, degradation homogeneity, thickness, and elasticity of the scaffold can be readily modified to yield an implant with a geometric structure that can be individually tailored to one of many physiological wound sites. The initial incarnation of the TAS scaffold is a collagen-glycosaminoglycan (GAG) copolymer scaffold with a mean pore size between 5 and 200 µm, preferably between 20 and 150 µm; relative density of 0.5-10%, preferably 0.5-5%; and a degradation half life of 1-6 weeks, preferably 1-4 weeks.

(viii) The TAS may be uniform in structure or developed in such a way that the sides or certain areas of it have different properties including, but not limited to, local areas of modified density, pore size, degradation rates, elasticity, and thickness. These may be particularly used for fixing the scaffold in place as well as maintaining the shape of the scaffold.

(ix) Optionally, the TAS may be provided with therapeutic and/or diagnostic agents, including, but not limited to, antibiotics, cytokines, non-steroidal anti-inflammatory drugs, fibrinolytic agents, and corticosteroids, prior to implantation. The porous nature of the TAS allows it to hold liquid agents much in the way (but not limited to) a traditional sponge holds water and deliver them to various areas of the body, such as to the area of injury. Although it is not required, the structure of the TAS may be modified in such a way that the lower part of the TAS that comes in a contact with the injured surface has higher permeability than the upper part and thus allows preferential optional therapeutic agent outflow from the TAS into the underlying wound area and inflow of exudate and cells through the lower part of TAS into the scaffold structure (FIG. 1).

(x) In its suggested incarnation, the TAS is constructed from components and subjected to processing conditions that render it both nonimmunogenic and nonantigenic.

The invention claimed is:

1. A device for inhibiting adhesion of apposing internal human body tissue layers, said device comprising:
a scaffold prepared by co-precipitation of collagen and a glycosaminoglycan (GAG), followed by lyophilization to produce a collagen-GAG scaffold having first and second collagen-GAG copolymer portions, wherein said first collagen-GAG copolymer portion has a first mean pore size, and said second collagen-GAG copolymer portion has a second mean pore size, with said first mean pore size being substantially smaller than said second mean pore size.

2. The device of claim 1 wherein said second collagen-GAG copolymer portion is substantially more liquid permeable than said first collagen-GAG portion.

3. The device of claim 1 wherein said scaffold has a predetermined degradation half life of between about 1 and 6 weeks when disposed in vivo.

* * * * *